US00PP29347P3

(12) United States Plant Patent
Lambert

(10) Patent No.: US PP29,347 P3
(45) Date of Patent: May 29, 2018

(54) ***AGAPANTHUS* PLANT NAMED 'BNA01'**

(50) Latin Name: *Agapanthus africanus*
Varietal Denomination: BNA01

(71) Applicant: Harold Lambert, Wauchula, FL (US)

(72) Inventor: Harold Lambert, Wauchula, FL (US)

( * ) Notice: Subject to any disclaimer, the term of this patent is extended or adjusted under 35 U.S.C. 154(b) by 0 days. days.

(21) Appl. No.: 15/330,069

(22) Filed: Aug. 1, 2016

(65) Prior Publication Data

US 2018/0035596 P1 Feb. 1, 2018

(51) Int. Cl.
*A01H 5/02* (2018.01)
*A01H 5/12* (2018.01)

(52) U.S. Cl.
USPC ..... Plt./398
CPC ..... *A01H 5/02* (2013.01); *A01H 5/12* (2013.01)

(58) Field of Classification Search
USPC ..... Plt./398
See application file for complete search history.

(56) References Cited

PUBLICATIONS

Dothan Nurseries Greenhouse and Gardens (facebook page) May 16, 2016 [online] [retrieved on Sep. 26, 2017 from the Internet] (1 page total).*
MarkWatch—'Indigo Princess' *Agapanthus*; https://markwatchplants.com/trademarks/indigo-princess-agapanthus [retrieved on Sep. 26, 2017 from the Internet] (1 page total).*

* cited by examiner

*Primary Examiner* — Susan McCormick Ewoldt
(74) *Attorney, Agent, or Firm* — Cassandra Bright

(57) ABSTRACT

A new and distinct *Agapanthus* cultivar named 'BNA01' is disclosed, characterized by a very stable, dark blue flower color. Plants show improved tolerance for extreme Summer heat, as observed in Florida, resisting foliage fading or burn. Plants may re-bloom during late Summer, after the initial large flush in late Spring. The new variety is a *Agapanthus*, typically produced as an outdoor ornamental plant.

1 Drawing Sheet

Latin name of the genus and species: *Agapanthus africanus.*

Variety denomination: 'BNA01'.

BACKGROUND OF THE INVENTION

The new cultivar is the product of chance discovery. The new variety originated as a naturally occurring, whole plant mutation of an unpatented, unnamed *Agapanthus africanus.*

The new variety was discovered by the inventor in a commercial planting of the unnamed *Agapanthus africanus* parent in Wauchula, Fla. The inventor identified a single, whole plant mutation at his commercial nursery in 2006. After isolating the interesting new plant, the inventor divided the original plant and subsequent propagules over several years, to establish stability.

Asexual reproduction of the new cultivar 'BNA01' was first performed by division in Wauchula, Fla., during 2006, on a very limited basis. Access to all plants was restricted, as plants were kept in a location not open to the public, at the inventor's nursery. Through subsequent propagation, multiple generations have been reproduced, which have shown that the unique features of this cultivar are stable and reproduced true to type.

SUMMARY OF THE INVENTION

The cultivar 'BNA01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BNA01'. These characteristics in combination distinguish 'BNA01' as a new and distinct *Agapanthus* cultivar:

1. Dark blue flower color.
2. Very stable dark flower color.
3. Observed to be more heat tolerant than typical for *Agapanthus africanus* grown in Florida during the Summer months. Heat tolerance exhibited in foliage which does not fade or scorch.
4. Easily and successfully reproduced by division.
5. Some re-blooming observed, after initial bloom period beginning in early Summer.

PARENT COMPARISON

Plants of the new cultivar 'BNA01' are similar to the parent in most horticultural characteristics. However, the new variety is more tolerant of extreme Summer heat than the parent variety, maintaining Summer foliage color better. Additionally, plants of 'BNA01' produce flowers of a darker blue than the parent variety, and have a longer bloom period.

COMMERCIAL COMPARISON

Plants of the new cultivar 'BNA01' are similar to the unpatented commercial variety *Agapanthus africanus* 'African Queen' in most horticultural characteristics. The new variety, however, differs in the following:

1. Longer bloom period than the comparator.
2. 'BNA01' produces darker blue flowers than this comparator.
3. Foliage of the new variety is more resistant to Summer heat than that of the comparator.
4. Plants of the new variety are on average 10 to 20 cm shorter.

Plants of the new cultivar 'BNA01' are similar to the commercial variety *Agapanthus africanus* 'Peter Pan', unpatented, in most horticultural characteristics. The new variety, however, differs in the following:

1. Plants of the new variety are taller than plants of 'Peter Pan' by 20 cm on average.
2. Flowers of the new variety are much darker blue than flower of 'Peter Pan'.
3. Plants of the new variety are more resistant to Summer heat, with foliage maintaining a deep green color without fading or burning.
4. Plants of the new variety are easier to propagate than plants of 'Peter Pan'.

BRIEF DESCRIPTION OF THE PHOTOGRAPH

The accompanying photograph in FIG. 1 illustrates in full color a typical plant of 'BNA01' grown in Loxley, Ala. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BNA01' plants grown outdoors in Loxley, Ala. Plants are approximately 1 year old. Temperatures ranged from approximately 4° C. to 25° C. at night and 10° C. to 35° C. during the day. No artificial light, photoperiodic treatments were given to the plants. No chemical treatments were given to plants. Measurements and numerical values represent averages of typical plant types.

Botanical classification: *Agapanthus africanus* 'BNA01'.

PROPAGATION

Root description: Thick, fleshy root system colored near Greyed-Orange 164D and Orange-White 159C.

PLANT

Growth habit: Clump forming tender perennial with arching, pendulous foliage.

Height: Foliar plane 38 cm. Flowering plane approximately 62 cm.

Plant spread: Approximately 70 cm.

Growth rate: Moderate.

Growth pattern: The plant grows throughout most of the year but mainly in the Spring and Summer months. This growth is in the form of basal shoots or pups as well as some leaf extension. From approximately early June, flowers start to appear and remain until approximately Late Summer, in the Southern United States.

FOLIAGE

Leaf:

- *Average leaf length*.—Average range approximately 21 to 32 cm.
- *Average leaf width*.—Average range approximately 1.8 to 2.8 cm.
- *Arrangement*.—Basal, irregular whorls.
- *Shape of blade*.—Linear.
- *Apex*.—Acute.
- *Base*.—Cuneate.
- *Margin*.—Entire.
- *Texture of top surface*.—Smooth.
- *Texture of bottom surface*.—Smooth.
- *Quantity of leaves per plant*.—Average 40 to 55.
- *Color*.—Mature and young foliage is the same color. Upper blade: Near Green 137A. Lower Blade: Near Green 137A.
- *Venation*.—Type: Linear. Venation color upper side: Indistinguishable from leaf blade. Venation color under side: Indistinguishable from leaf blade.

FLOWER

Natural flowering season: Beginning in late Spring, lasting until mid to late Summer, in the Southern United States.

Length of flowering period: Approximately 9 to 12 weeks. A lesser amount of flower spikes may be produced late Summer, after the initial flower.

Inflorescence type: Terminal Umbel with approximately 30 individual flowers and approximately 10 buds. Approximately 8 to 14 umbels produced during the peak flowering season.

Individual flower type: Single.

Flower profile: Funnelform.

Bud:

- *Shape*.—Ovate.
- *Shape*.—Narrow ovate.
- *Length*.—Approximately 1.7 cm.
- *Diameter*.—Approximately 0.7 cm.
- *Color*.—Near Violet-Blue N89C, apex near N89A. Base near Violet N88D.

Umbel size:

- *Diameter*.—Average 14 cm.
- *Height*.—Average 7 cm.

Corolla:

- *Arrangement*.—Apetalous, single, campanulate flowers composed of 6 basally fused tepals, shaped into a flared trumpet.
- *Size*.—Length: Approximately 3.5 cm. Width: Approximately 1.9 cm at widest point. Lobe Length: Approximately 2.1 cm. Lobe Width: Average range 0.7 to 0.9 cm.
- *Margin*.—Entire.
- *Shape*.—Lanceolate.
- *Apex*.—Broadly acute.
- *Texture*.—Glabrous all surfaces.

Color:

- *Tepals*.—When opening: Outer surface: Near Violet-Blue N89A. Inner surface: Near Violet N88A. Fully opened: Outer surface: Near RHS Violet-Blue N89C, with center streak near 91A. Inner surface: Near RHS Violet-Blue N89A, with large center streak near 91A. Color Changes when Aging: Outer surface: Near RHS Violet-Blue N89A, with large center streak near 91A. Inner surface: Near RHS Violet-Blue N89B, with faint center streak near 91A.

*Sepals*.—Not present.

Fragrance: Faint musty scent.

Pedicels:

*Length*.—Average range 2.5 to 3.0 cm.

*Width*.—Approximately 0.2 cm.

*Aspect*.—Somewhat undulating.

*Color*.—Near RHS Green 137A, lower surface. Upper surface near Yellow-Green 147A, slightly flushed Greyed-Purple N186A.

Scape:

*Length*.—Average 50 cm.

*Width*.—Approximately 0.7 to 0.9 cm.

*Angle*.—Upright from center of plant, mainly straight, with slight curvature.

*Strength*.—Very strong.

*Color*.—Near RHS Green 137A, very slightly flushed near Greyed-Purple N186A.

Flower filament color: Near Violet-Blue RHS 90A, lower section near 91A.

Flower anther color: Near Greyed-Purple N186A.

Flower style color: Near Violet-Blue RHS 90C, lower section near 91C.

REPRODUCTIVE ORGANS

Stamens:

*Number*.—Average 6.

*Filament length*.—Approximately 2.1 cm.

*Filament color*.—Near Violet-Blue RHS 90A, lower section near 91A.

*Anther length*.—0.2 cm.

*Anther color*.—Near Greyed-Purple N186A.

*Pollen*.—Scant, colored near Violet-Blue 91C.

Pistil:

*Number*.—1.

*Length*.—Approximately 2.8 cm.

*Style color*.—Near Violet-Blue RHS 90C, lower section near 91C.

*Stigma*.—Shape: Linear. Color: Near RHS Violet-Blue 91A.

*Ovary color*.—Near RHS Yellow-Green 145B.

OTHER CHARACTERISTICS

Seed production: Seed production not observed to date.

Disease resistance: Neither resistance nor susceptibility to normal diseases and pests of *Agapanthus*.

Temperature tolerance: Typically USDA zones 7b through 11.

Drought tolerance: Will tolerate considerable dryness once established.

What is claimed is:

1. A new and distinct cultivar of *Agapanthus* plant named 'BNA01' as herein illustrated and described.

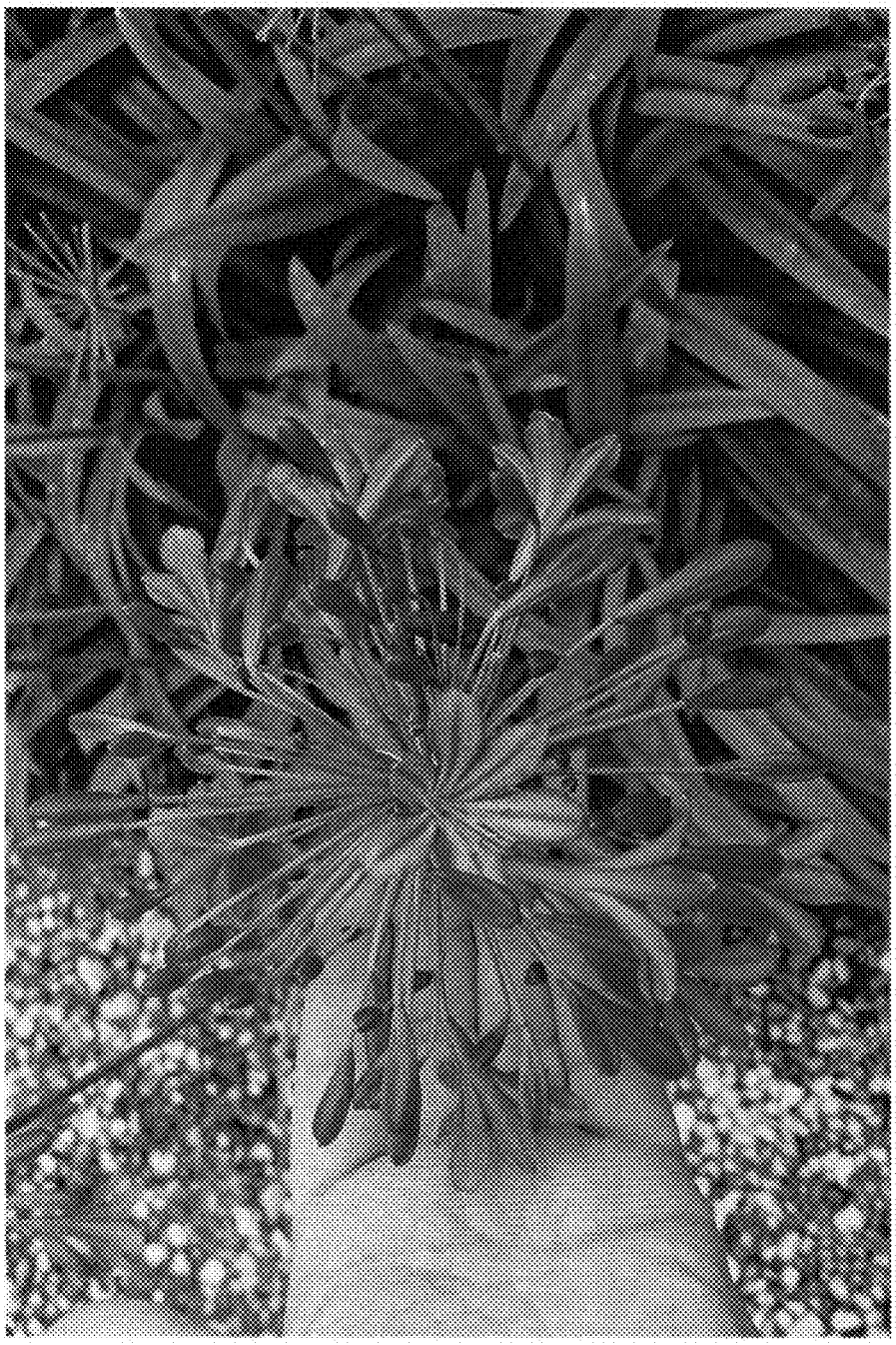

* * * * *